(12) United States Patent
Weilbacher et al.

(10) Patent No.: US 6,217,544 B1
(45) Date of Patent: Apr. 17, 2001

(54) FILTRATION VALVE CAP WITH REFLUX CLEARING FEATURE AND RELATED METHOD OF USE THEREOF

(75) Inventors: Eugene E. Weilbacher, Ellisville; Jacky S. Yam, St. Louis, both of MO (US)

(73) Assignee: Sherwood Services, AG, Schaffhausen (CH)

( * ) Notice: Subject to any disclaimer, the term of this patent is extended or adjusted under 35 U.S.C. 154(b) by 0 days.

(21) Appl. No.: 09/206,068

(22) Filed: Dec. 4, 1998

Related U.S. Application Data (62) Division of application No. 08/866,731, filed on Apr. 30, 1997, now Pat. No. 5,891,117.

(51) Int. Cl.[7] ................................................. A61M 37/00
(52) U.S. Cl. ................................................. 604/28; 604/4
(58) Field of Search ........................ 604/4–6, 317–321, 604/405, 406, 28

(56) References Cited

U.S. PATENT DOCUMENTS

| | | | |
|---|---|---|---|
| 3,896,733 | 7/1975 | Rosenberg | 128/214 R |
| 3,929,133 | 12/1975 | Ragab | 128/277 |
| 4,033,345 | 7/1977 | Sorenson | 128/214 R |
| 4,157,965 | 6/1979 | Raible | 210/305 |
| 4,402,687 | 9/1983 | Denty et al. | 604/319 |
| 4,443,220 | 4/1984 | Hauer et al. | 604/408 |
| 4,631,050 | 12/1986 | Reed et al. | 604/4 |
| 4,798,578 | 1/1989 | Ranford | 604/4 |
| 4,923,438 | 5/1990 | Vasconcellos et al. | 604/4 |
| 4,923,451 | 5/1990 | McCormick | 604/321 |
| 4,954,251 | 9/1990 | Barnes et al. | 210/806 |
| 4,981,596 | 1/1991 | Shiino et al. | 210/650 |
| 4,988,342 | 1/1991 | Herweck et al. | 604/321 |
| 5,024,613 | 6/1991 | Vasconcellos et al. | 604/4 |
| 5,055,198 | 10/1991 | Shettigar | 210/650 |
| 5,078,688 | * 1/1992 | Lobodzinski et al. | 604/164 |
| 5,114,416 | 5/1992 | Karwoski | 604/321 |
| 5,141,504 | * 8/1992 | Herweck et al. | 604/317 |
| 5,149,325 | 9/1992 | Telang | 604/119 |
| 5,269,924 | 12/1993 | Rochat | 210/445 |
| 5,354,262 | * 10/1994 | Boehringer et al. | 604/4 |
| 5,372,593 | 12/1994 | Boehringer et al. | 609/319 |
| 5,439,587 | 8/1995 | Stankowski et al. | 210/321.64 |
| 5,496,299 | * 3/1996 | Felix et al. | 604/319 |
| 5,772,625 | * 6/1998 | Krueger et al. | 604/9 |
| 5,837,229 | * 10/1998 | Auth et al. | 604/171 |
| 5,931,821 | * 8/1999 | Weilbacher et al. | 604/321 |

\* cited by examiner

*Primary Examiner*—John G. Weiss
*Assistant Examiner*—David J. Cho
(74) *Attorney, Agent, or Firm*—Mark S. Leonardo; Brown, Rudnick, Freed & Gesmer, P.C.

(57) ABSTRACT

A progressive filtration system for a chest drainage unit during continuous autotransfusion that allows the user to clear the fluid pathway of blood clots and trapped air that form after filtration in a flushing action initiated by the user. The filtration system comprises a gross filter for filtering incoming blood at the inlet portion of a collection chamber of a chest drainage unit and a fine filter assembly located at the bottom portion of the collection chamber for refiltering collected blood prior to reinfusion of that blood back to the patient. The filter assembly includes a valve cap at the top portion of the assembly that functions as a one way valve that permits reflux of later developing blood clots that might clog the tubing once the blood has already passed through the assembly. The valve cap is also adapted for sealing engagement with a drop tube that places the filter assembly in fluid flow communication with an outlet of the collection chamber located at the top portion of the chamber.

3 Claims, 8 Drawing Sheets figure 1
(PRIOR ART)

Figure 2 figure 3 figure 4 figure 5 figure 6 figure 7 figure 8 figure 9

FILTRATION VALVE CAP WITH REFLUX CLEARING FEATURE AND RELATED METHOD OF USE THEREOF

This application is a divisional of patent application Ser. No. 08/866,731 filed on Apr. 30, 1997, now U.S. Pat. No. 5,891,117.

BACKGROUND TO THE INVENTION

1. Field of the Invention

The present invention relates to a system for flushing out contaminants that clog the fluid pathway of an autotransfusion system, and more specifically to a filtration system for a chest drainage unit (CDU) that includes a valve means for generating a reflux action that clears large blood clots that form in the fluid pathway. More particularly, this invention relates to a flow-sensitive valve cap and related method of use for flushing large blood clots back into the CDU's collection chamber while preventing re-entry of the same into the fluid pathway.

2. Prior Art

A CDU is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various infections can cause a build up of liquid and gases around the lungs in the intrapleural space. When this happens, it causes the lungs to collapse to a volume much less than that of the pleural cavity, thereby severely impairing breathing functions of the patient. The lungs can be re-expanded to their normal state to fill the pleural cavity by draining the liquid and gases from the intrapleural space using a chest drainage unit.

CDUs are also used during autotransfusion for recovering autologous blood from the patient's pleural and mediastinal cavities and transfusing that blood back into the patient. Autotransfusion offers significant advantages over normal transfusion procedures which use homologous blood from other humans. Autologous blood reduces the risk of adverse reactions and transmission of infectious disease while supplying a readily available and safe source of compatible blood to the patient. For these reasons, CDUs are being designed to both evacuate fluids from the intrapleural space and autotransfuse shed autologous blood back into the patient.

Various devices have been developed to drain and collect fluids such as blood from the intrapleural space for subsequent autotransfusion. U.S. Pat. No. 4,114,416 to Karwoski et al. illustrates the prior art development of autotransfusion chest drainage units. The device includes a collection chamber for the collection of fluid from the pleural cavity, a water seal chamber for preventing passage of gas from the atmosphere into the patient's pleural and mediastinal cavities, and a manometer chamber for regulating the degree of vacuum in the system. An inlet port of the collection chamber is connected to the patient's pleural cavity via a thoracotomy tube that deposits shed blood and gases into the collection chamber. As the shed blood enters the inlet portion of the collection chamber, a large area gross filter, such as a fabric or an open-pore foam filter, is used to remove blood clots and gross particles from incoming fluids. Once filtered, the blood collects at the bottom portion of the collection chamber until reinfusion is effected and the blood is drained through an outlet port located at the bottom portion of the collection chamber. The Karwoski et al. device is also placed in fluid flow communication with a blood compatible pump set through tubing that connects the pump to the outlet port and permits the collected blood to drain therethrough for reinfusion to the patient.

One drawback with the Karwoski et al. device is that no provision is made for clearing out blood clots that develop after the blood has been filtered and pumped from the collection chamber. In some instances, large blood clots may form even after the blood has been filtered prior to reinfusion back to the patient. If these clots are not removed or cleared out when the blood is reinfused back to the patient from the CDU, the fluid pathway between the patient and the filtration site inside the CDU will become clogged and unusable as the blood exits the Karwoski et al. device. Further, a microaggregate filter that is normally interposed between the outlet of the collection chamber and the patient can also become clogged with blood clots and unusable. As a result, a practitioner will have to take the time to replace the entire CDU as well as the blood infusion set and attendant tubing which exposes the patient to undesirable risks caused by the time delay in clearing or replacing the fluid pathway between the CDU and the patient while reestablishing the autotransfusion process. Moreover, interruption of the autotransfusion process might require the practitioner to substitute homologous blood that could be contaminated or incompatible with the patient's own blood.

As of yet, nothing in the prior art has addressed the problem of unclogging the fluid pathway between the filtration site and the patient of blood clots that form after filtration. Specifically, there has been no design consideration that permits the practitioner to use the CDU as a means for clearing out clogged tubing of blood clots without a major interruption of the autotransfusion process. Further, there has been no procedural consideration setting forth a method for clearing out the fluid pathway of blood clots after the blood has passed through the filtration site during reinfusion to the patient.

There therefore exists a need in the art for a filtration system that includes a valve cap in combination with a spike port assembly that permits the practitioner to employ a method of clearing out blood clots that develop after filtration without major interruption of the autotransfusion process.

BRIEF SUMMARY AND OBJECT OF THE INVENTION

In brief summary, the present invention overcomes and substantially alleviates the deficiencies in the prior art by providing a progressive filtration system that provides a valve means and related method of use thereof for clearing the fluid pathway between the filtration site and the patient of blood clots that have formed after filtration. The filtration system of the present invention comprises a gross filter for filtering incoming blood at the inlet portion of the collection chamber and a conventional fine filter assembly located at the bottom portion of the collection chamber that refilters collected blood prior to reinfusion of that blood back to the patient. The filter assembly includes a valve cap at the top portion of the assembly that functions essentially as a one way valve that permits reflux of blood clots that might clog the fluid pathway once the blood has passed through the assembly. The valve cap also functions as an additional filtration site to the filter assembly when the valve cap is not being used during the reflux operation. Further, the valve cap is adapted for sealing engagement with a drop tube that places the filter assembly in fluid flow communication with the outlet of the collection chamber located at the top portion of the chamber. Finally, the present invention provides for a method of clearing the fluid pathway using a spike port interposed and in fluid flow communication between the CDU and the patient. In combination with the valve cap, the practitioner uses the spike port for initiating a reflux action that flushes blood clots through the valve cap and back into the collection chamber.

Accordingly, it is the principle object of the present invention to provide an apparatus that includes a reliable and efficient filtration system that allows the practitioner to clear blood clots and other contaminants from the fluid pathway without a major interruption of the autotransfusion process.

Another object of the present invention is to provide a valve device in combination with a spike port for providing a means for flushing out blood clots from the fluid pathway that form after the filtration process.

A further object of the present invention is to provide a method for flushing back blood clots into the collection chamber that clog the fluid pathway between the filtration site and the patient.

These and other objects of the present invention are realized in a presently preferred embodiment thereof, described by way of example and not necessarily by way of limitation, which provides for a filtration system that includes a valve cap and spike port for clearing the fluid pathway between the filtration site and the patient of blood clots and a related method of use thereof.

DETAILED DESCRIPTION

As shown in the exemplary drawings for the purposes of illustration, an embodiment of the continuous autotransfusion filtration system made in accordance with the principles of the present invention, referred to generally by reference 10, is provided for the refiltering of collected blood deposited at the bottom portion of chest drainage unit's collection chamber prior to reinfusion of that blood back to the patient.

Figure 1:
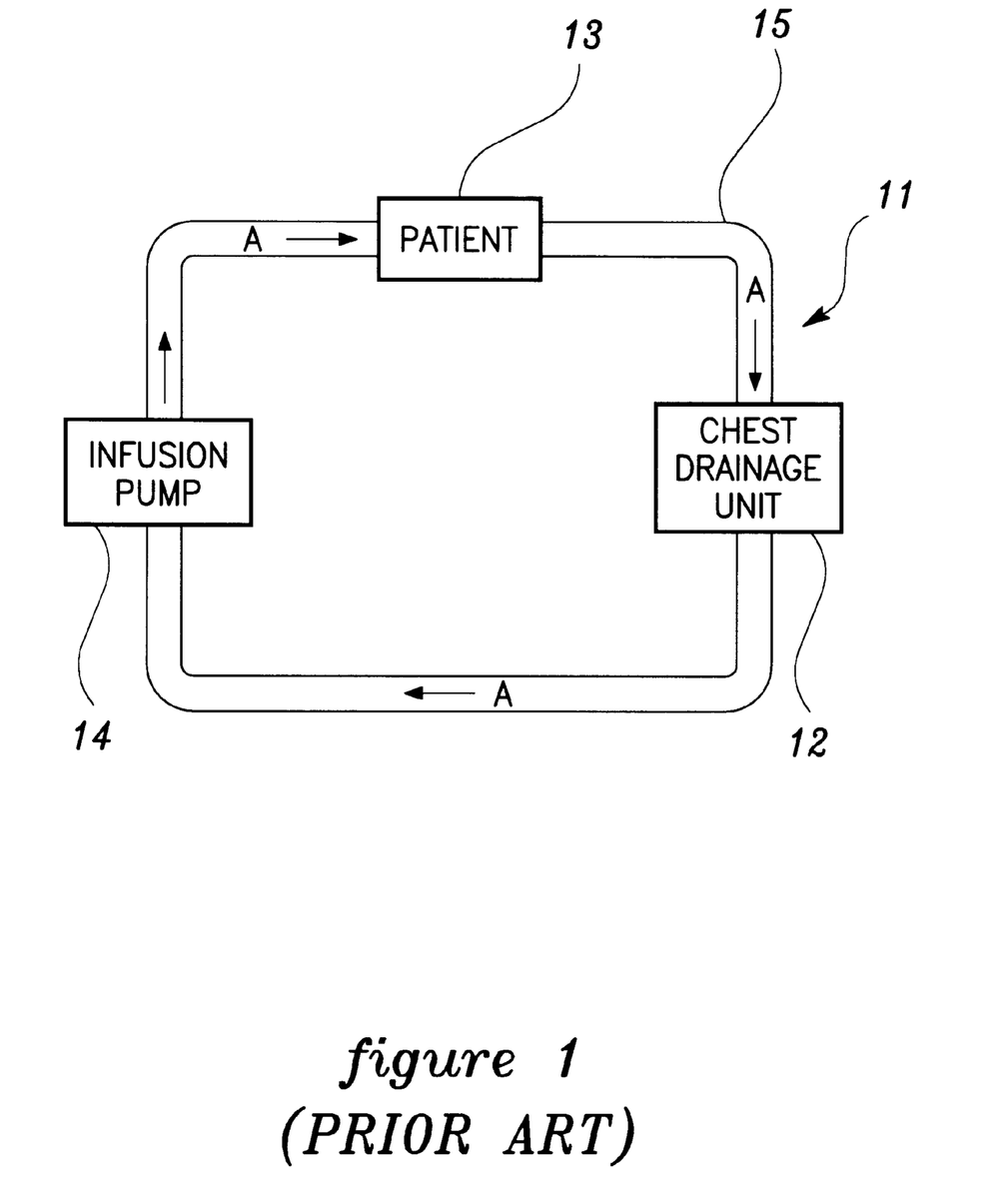
FIG. 1 is a simplified block diagram showing the basic operation of a prior art autotransfusion system.

A prior art continuous autotransfusion system is shown in FIG. 1. The basic configuration of an autotransfusion system 11 comprises a CDU 12 for sterile collection and if desired, transfer of shed fluids from a patient 13, a blood compatible infusion pump 14 placed in fluid flow communication with CDU 12 for reinfusing shed blood back to patient 13, and infusion tubing 15 for use as a conduit to transfer the blood between autotransfusion system 11 and patient 13. Liquid flow A denotes the direction of the fluid flow within system 11.

The basic operation of autotransfusion system 11 is disclosed in U.S. Pat. No. 4,798,578 to Ranford and is herein incorporated by reference in its entirety. In short summary, autotransfusion system 11 operates by using CDU 12 for the sterile collection of blood and fluids drawn from patient 13, and simultaneous reinfuses the fluids back to the circulatory system of patient 13.

Figure 2:
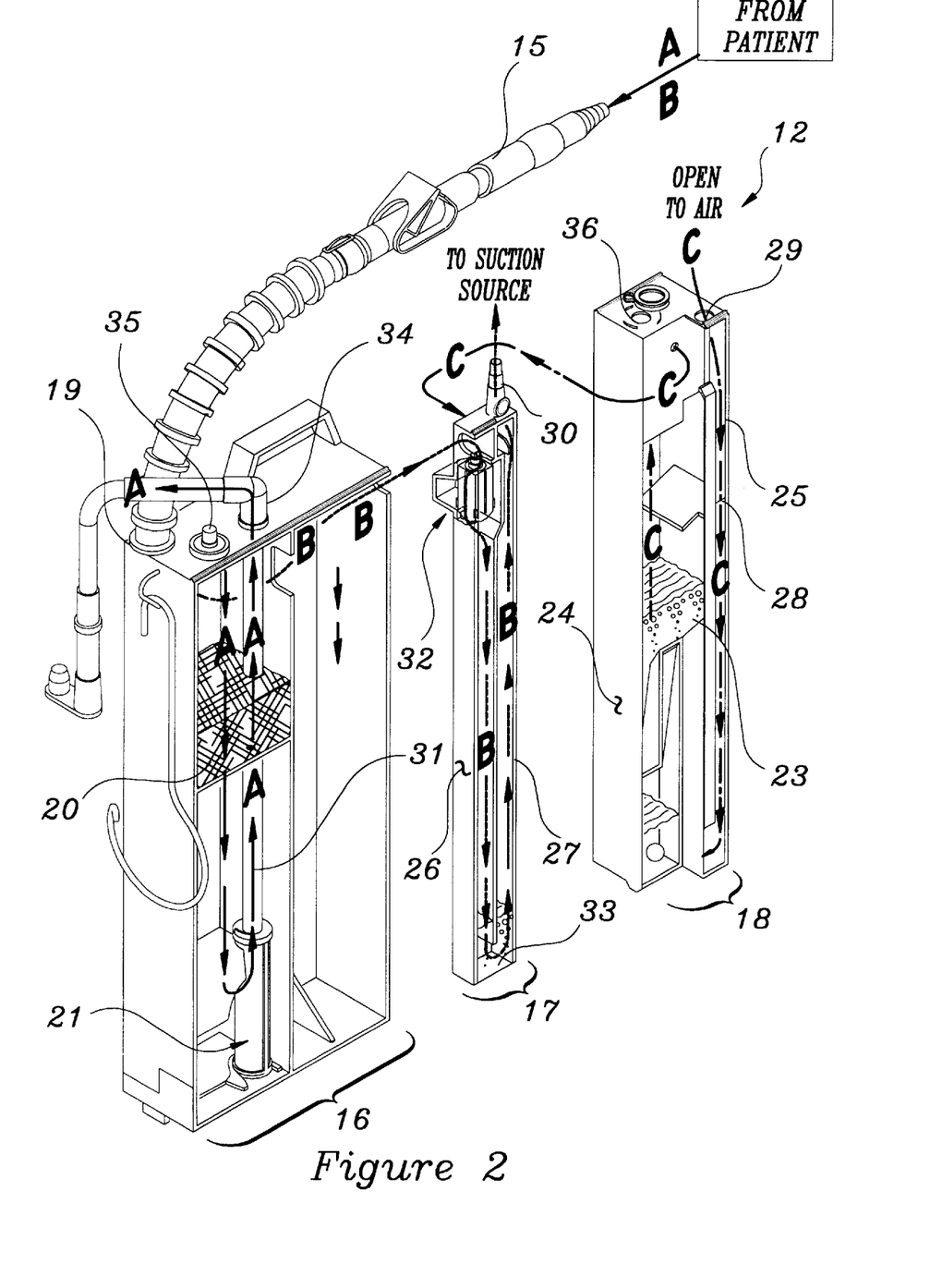
FIG. 2 is a partial cross section showing an exploded view of an autotransfusion chest drainage unit according to the present invention.

The general process of autotransfusing a patient's blood begins by drawing fluids from the patient's pleural and mediastinal cavities using a suction source (not shown) located at CDU 12 to create a positive liquid flow A through the autotransfusion system 11. The suction source forces shed body fluids from patient 13 through infusion tubing 15 and into the collection chamber (not shown) of CDU 12. Referring to FIG. 2, as fluid enters collection chamber 16 at inlet port 19, it is run through a gross filter 20 which traps macroscopic debris such as blood clots, bone fragments and the like that become entrained in blood or other body fluids. Once the fluid is filtered, it is temporarily stored in collection chamber 16 before being pumped out of chamber 16 by infusion pump 14 where the blood is reinfused back to patient 13 through infusion tubing 15, thereby finishing one complete autotransfusion cycle. Infusion tubing 15 may be made of any suitable flexible plastic material, for example polyurethane or PVC, for use in transmitting fluids and gas throughout system 11.

The operative features of CDU 12 in accordance with the present invention will be discussed in greater detail as best illustrated in FIG. 2. An autotransfusion CDU 12 consists of a standard three chamber unit found in the prior art comprising a collection chamber 16, a water seal chamber 17 and suction control chamber 18. Collection chamber 16 is designed to receive fluids and gases drained from the patient's pleural and mediastinal cavities, but it may also function as a filtration site to filter blood and other fluids of unwanted debris. In an alternative embodiment, CDU 12 may be configured to have an additional second collection chamber (not shown) separate from the CDU 12 body which acts as the filtration site while the collection chamber 16 inside CDU 12 acts as an overflow chamber for the second detached chamber, as disclosed in the aforementioned Ranford patent.

The other two chambers, the water seal chamber 17 and suction control chamber 18, serve to control and regulate the liquid flow A inside the collection chamber 16 as well as the pressure inside CDU 12. The suction control chamber 18 provides regulation of negative pressure during operation. Negative pressure within the CDU 12 is controlled by the height of water 23 contained in the suction control chamber 18 which insures a continuous suction of the pleural cavity and also alleviates concerns over possible tissue invagination in the thoracic catheter during high levels of negative pressure within the cavity.

As further shown in FIG. 2, the suction control chamber 18 consists of a U-shaped chamber having first and second arms 24, 25 respectively. A column of water 23 fills the bottom portion of the suction control chamber 18 and extends upward through both arms 24, 25. First arm 24 is in communication with both a second arm 27 of the water seal chamber 17 and a suction source (not shown) while the second arm 25 is open to atmospheric air which maintains an area of atmospheric pressure inside the arm 25 above a water line 28. Air flow C denotes the air flow throughout the suction control chamber 18. Air flow C shows atmospheric air being pulled into the second arm 25 through an open port 29 and into first arm 24 where it exits arm 24 through a suction port 30 towards the suction source. The height of the column of water 23 interposed between the first arm 24 exposed to vacuum source pressure and the second arm 25 which is at atmospheric pressure determines the level of negative pressure inside the collection chamber 16 and water seal chamber 17. For example, 20 cm of water 23 at the column translates to a negative pressure of −20 cm inside the collection chamber 16. U.S. Pat. No. 4,439,190 to Protzmann et al. gives a more detailed description of a typical suction control chamber of CDU 12 and its operation is herein incorporated by reference.

Water seal chamber 17 prevents reflux of air and fluid back to the patient by preventing the reentry of air and fluid into collection chamber 16 using an air sensitive, buoyant valve 32 in combination with a water seal 33. A detailed description of valve 32 is disclosed in the applicants' co-pending patent application No. 09/205,909 and its operation is herein incorporated by reference. As shown in FIG. 2, the air flow B is created by applying the source of suction to suction port 30 located at the top of water seal chamber 17. The applied suction creates an air flow B that forces fluid from the patient's body (not shown) through infusion tubing 15 and into the top portion of collection chamber 16 at an inlet port 19 where air flow B passes through an opening 34 and into water seal chamber 17. Once inside water seal chamber 17, air flow B travels down a first arm 26 and through water seal 33 located at the bottom portion of chamber 17. After passing through water seal 33, air flow B travels up a second arm 27 where it exits at suction port 30. Thus, air flow B creates a positive flow path that forces gases out of collection chamber 16 and through water seal 33 where these gases are removed from CDU 12 through suction port 30.

First arm 26 of water seal chamber 17 is in fluid flow communication with second arm 27 through water seal 33 at one end and collection chamber 16 at the other end, while second arm 27 is in fluid flow communication with first arm 26 at one end and suction control chamber 18 at its other end respectively. Water seal 33 functions as a protective one way valve that allows air to escape from collection chamber 16, while preventing contaminated atmospheric air from reentering the pleural cavity of the patient. By interposing a water seal 33 at the bottom portions of both first and second arms 26, 27, fluid is prevented from passing back through water seal 33 due to the difference in pressure maintained between the two arms 26, 27, thus preventing a reflux action. The importance in preventing reflux is that under certain respiratory conditions, a sudden increase in pressure within the pleural cavity can appear. For example, an air leak in the pleural cavity can interfere with the normal respiratory function of the patient's lungs. Finally, the bubbling action shown in water seal 33 represents evacuated air from collection chamber 16 that has passed through seal 33 into second arm 27.

In addition to water seal 33, which prevents any reflux of gases back into the collection chamber 16, an air flow sensitive, buoyant valve 32 is provided at the top portion of water seal chamber 17 as a further safeguard. CDU 12 is also designed so that air can escape through an automatic positive pressure relief valve 35 when an overpressure condition occurs inside the patient's pleural cavity, e.g. when the patient coughs. The automatic positive relief valve 35 is positioned on the top outside portion of CDU 12 and is in fluid flow communication with the suction control chamber 18. Similarly, collection-chamber 16 has a negative pressure relief valve 36 which manually vents excess negative pressure from the patient's pleural cavity when actuated by a nurse.

During autotransfusion, blood collected from the patient's pleural and mediastinal cavities travels through infusion tubing 15 where the blood enters the collection chamber 16 through inlet port 19. As the blood enters through inlet port 19 it falls through a gross filter 20 that removes clots and other contaminants from the blood. Once filtered, the blood collects at the bottom portion of collection chamber 16 where it is again refiltered using a filter assembly 37 prior to reinfusion. As the blood is refiltered through filter assembly 37, it runs up through a drop tube 31 that is attached to assembly 37 and exits at outlet port 22. In the preferred embodiment, outlet port 22 is located at the top portion of CDU 12. In alternative embodiments, the egress of blood through outlet port 22 can be from any suitable site along the surface of collection chamber 16 where the infusion tubing 15 may be attached to outlet port 22.

Figure 3:
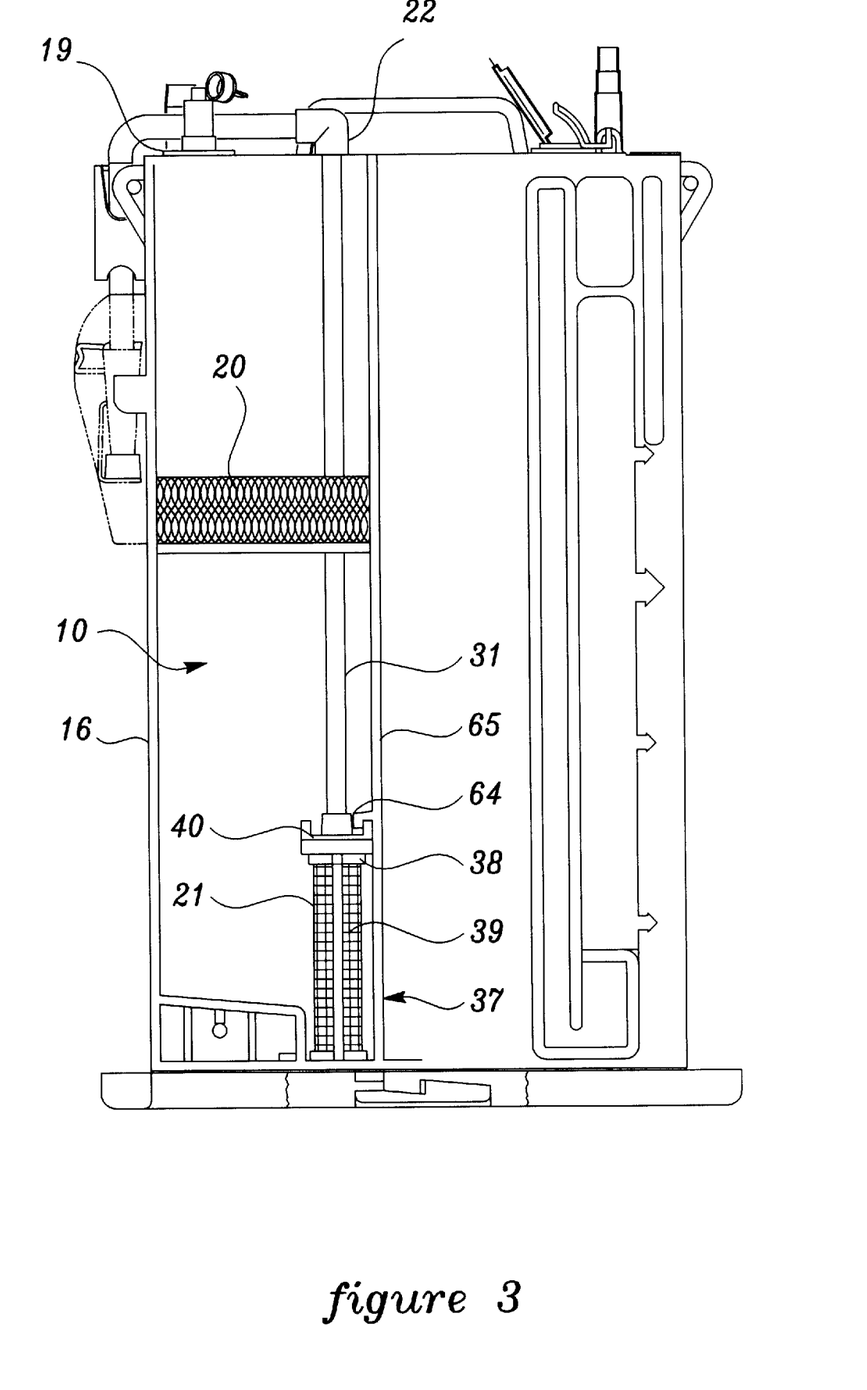
FIG. 3 is a front view of the micron filter according to the present invention.

Referring to FIG. 3, a more detailed description of the filtration system 10 in accordance with the present invention will be discussed. Filtration system 10 provides dual filtration of shed blood at both the inlet and outlet portions of collection chamber 16 and comprises gross filter 20, filter assembly 37 and drop tube 31 that places assembly 37 in fluid flow communication with outlet port 22. Gross filter 20 is interposed between the inlet port 19 and filter assembly 37 and serves to remove blood clots, bone, fat and bowel contents that become entrained in the blood as the blood enters from inlet port 19. Preferably, gross filter 20 is a large area gross filter, such as a fabric or an open-pore sponge filter, that is suitable for removing blood clots and gross particulates from blood.

Once the blood begins to fill the bottom portion of collection chamber 16, it is refiltered by filter assembly 37 as it exits chamber 16 for reinfusion back to the patient. Filter assembly 37 includes a fine filter 21 for removal of formed clots and a valve cap 38 that is attached to the top portion of filter 21. Valve cap 38 functions both as a retaining member for securing drop tube 31 as well as a one way valve for clearing out later forming blood clots that may clog either drop tube 31 or infusion tubing 15 leading from the collection chamber 16 once the blood has been filtered through fine filter 21.

Figure 4:
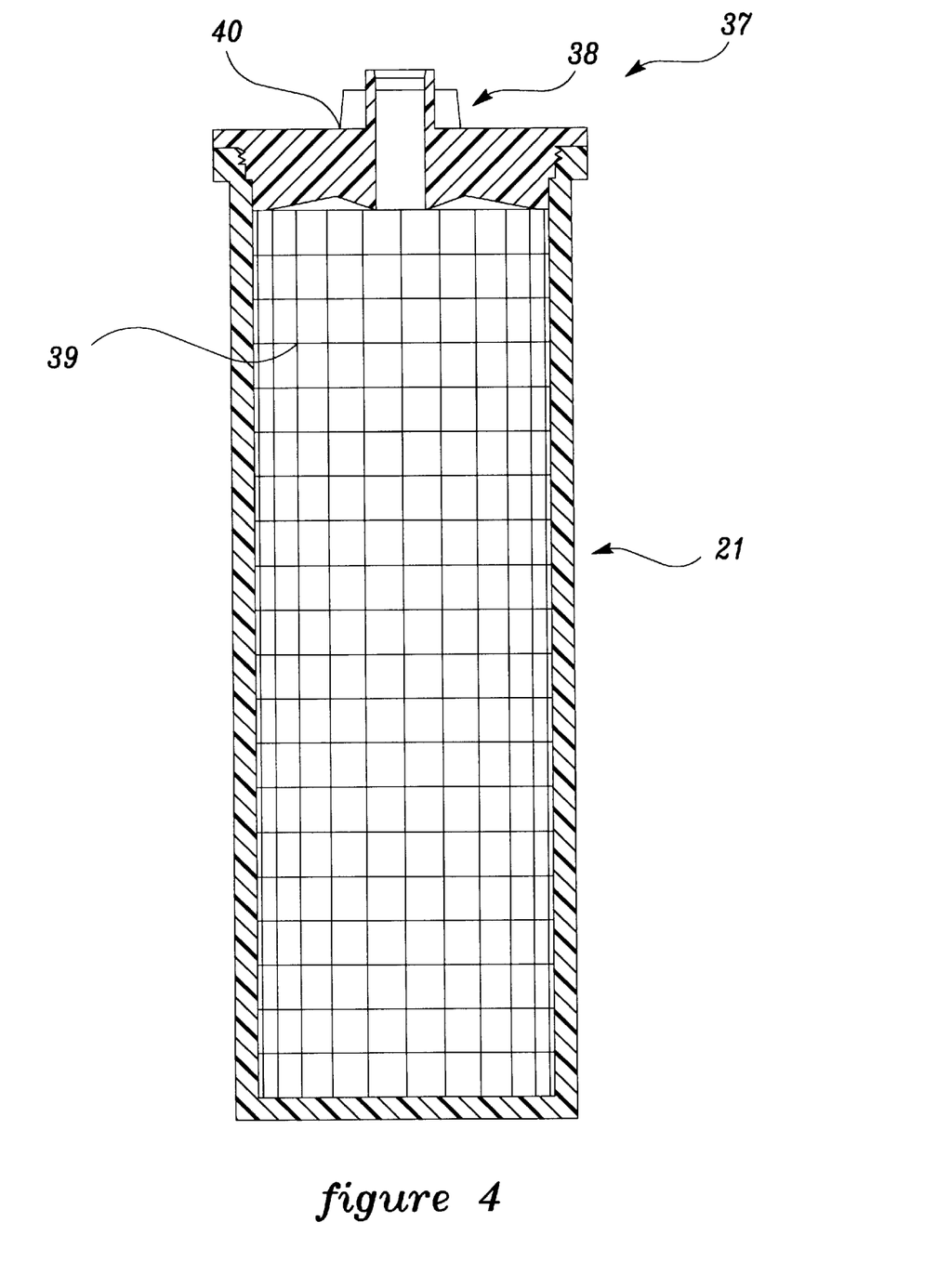
FIG. 4 is a cross section view of the filter body and valve cap according to the present invention.

Referring to FIG. 4, a more detailed description of filter assembly 37 will be discussed. As mentioned briefly above, filter assembly 37 comprises a fine filter 21 and valve cap 38. Fine filter 21 functions as a secondary filtration site for removing blood clots that form after filtration through gross filter 20 as the blood sits and collects at the bottom portion of collection chamber 16 prior to reinfusion. A micron polyester screen 39 is provided around substantially the entire surface area of fine filter 21 and provides a small pore size media for removing blood clots that form inside the collection chamber 16. Preferably, fine filter 21 is a model 991-66 high flow blood filter with a 210 micron screen manufactured by CUTTER BIOLOGICAL of Berkeley, Calif., however any suitable blood filter with a micron screen ranging from 40 to 210 microns is felt to fall with the scope of the present invention.

Figure 5:
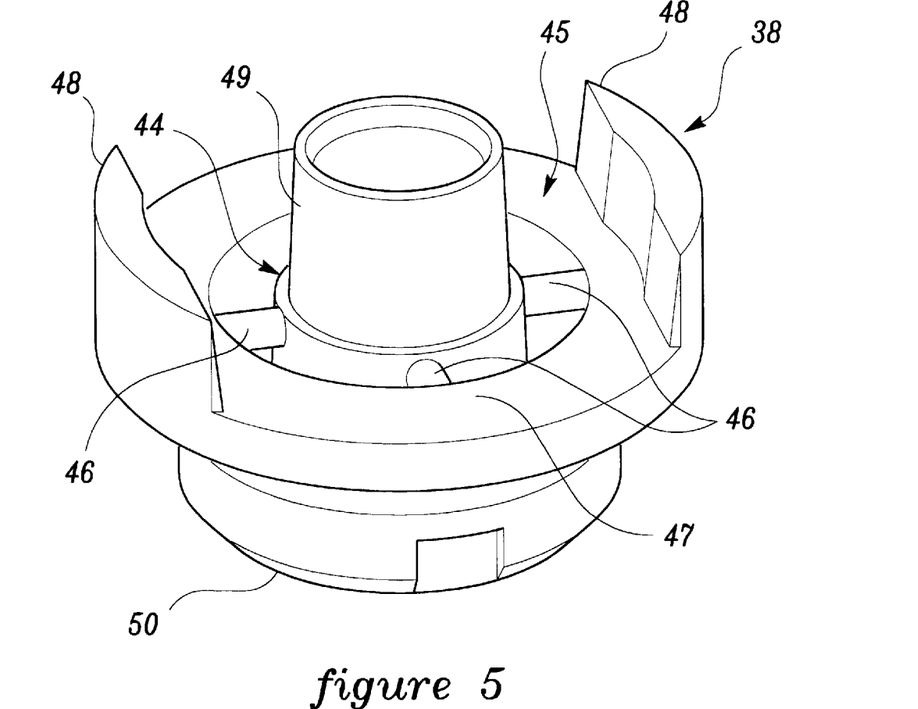
FIG. 5 is a perspective view of the valve cap according to the present invention.

With reference to FIG. 5, a more detailed description of valve cap 38 will be discussed. Valve cap 38 is attached to the top portion of fine filter 21 and has an annular shape with an inner portion 44 concentrically attached to an outer portion 45 by a plurality of partition members 46. In the preferred embodiment, inner portion 44 has four partition members 46 connecting it to outer portion 45, however any number of partition members 46 suitable for securely connecting the two portions 44, 45 together while leaving sufficient space for fluid flow therethrough is felt to fall within the scope of the present invention. Outer portion 45 forms two retaining members 48 in which either member 48 may be attached to an elbow 64 (shown in FIG. 3) on the side wall 65 (also shown in FIG. 3) of collection chamber 16 for retaining filter assembly 37 in place and preventing any vertical movement of assembly 37. Outer portion 45 also forms a plug member 50 at its bottom part for engaging the top portion of filter assembly 37.

Figure 6:
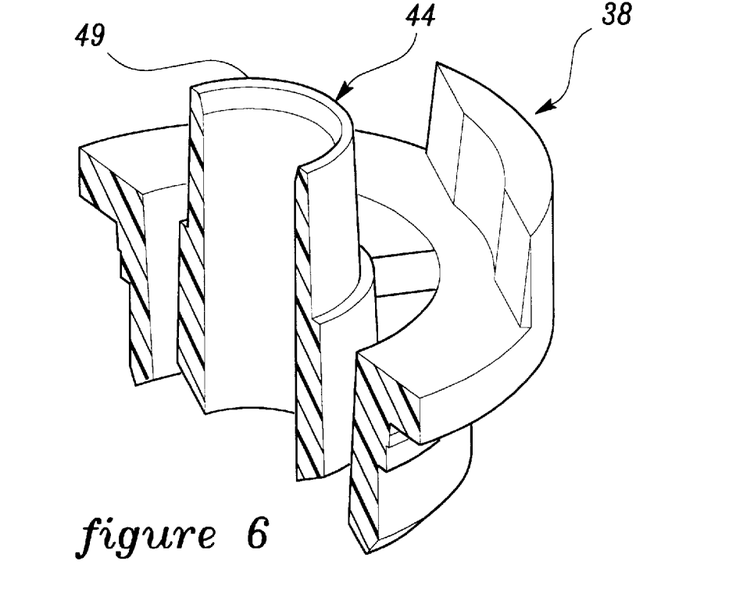
FIG. 6 is a section pictorial of FIG. 5 according to the present invention.
Figure 9:
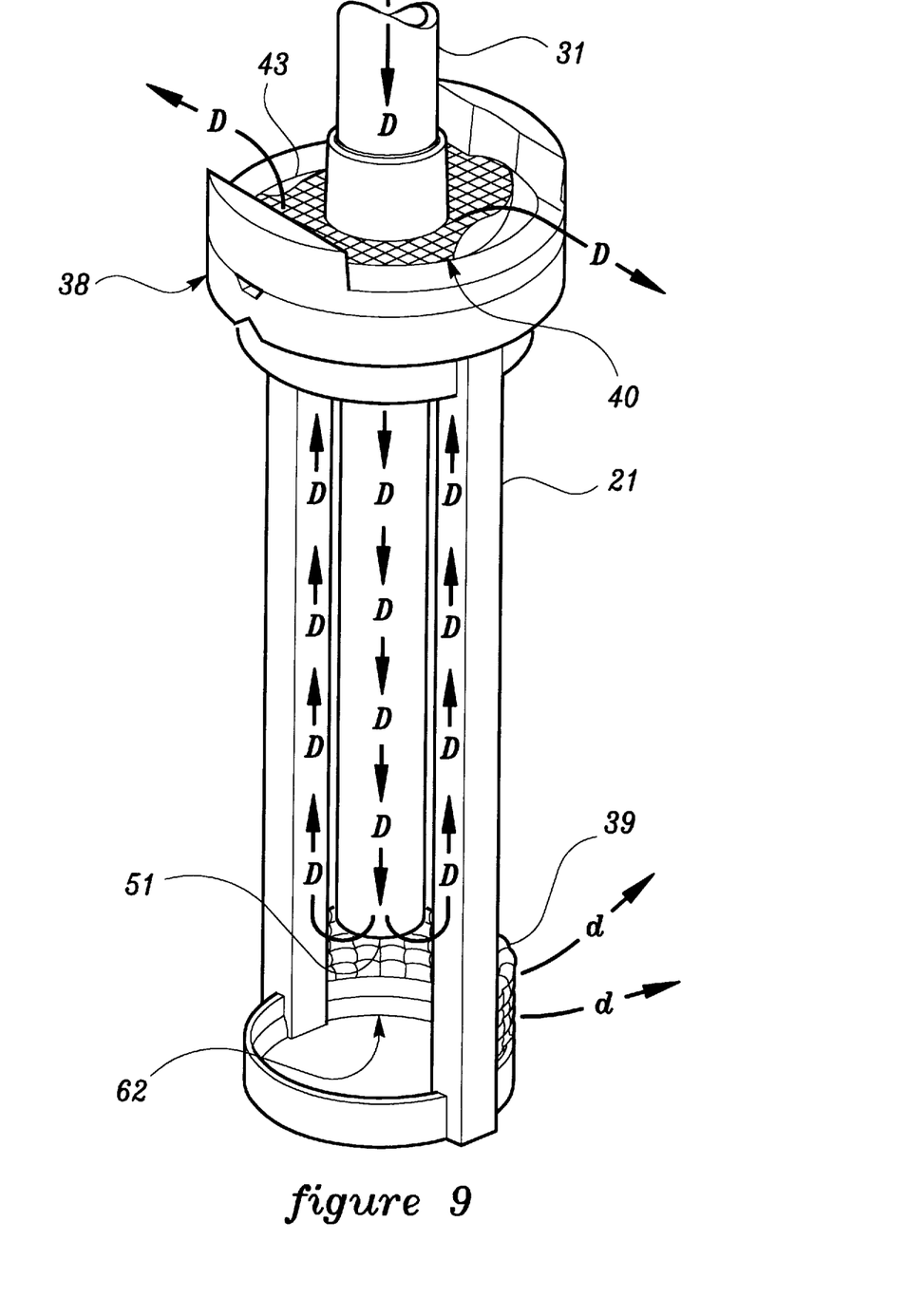
FIG. 9 is a perspective view of the filter assembly with a partial rendering of the polyester screen for illustrating the flushing action shown in FIG. 8.

Referring to FIG. 6, a cross section of valve cap 38 showing inner portion 44 is illustrated. Inner portion 44 forms a cylindrical bore 49 that is adapted to receive and align drop tube 31 with the elbow 64 extending from the side wall 65. During manufacturing, drop tube 31 is attached to outlet port 22 at its distal end while the proximal end of tube 31 is aligned and secured through cylindrical bore 49. With reference to FIG. 9, the proximal end of drop tube 31 forms a collection opening 51 that is confined inside filter assembly 37 and is spaced approximately ⅜ inch off the collection chamber floor (not shown). Collection opening 51 provides an inlet for receiving fluid flow therein during the filtration process wherein collected blood is forced through opening 51 and into drop tube 31 for reinfusion to patient 12. As mentioned above, collection opening 51 is preferably spaced ⅜ inch off the collection chamber floor 52, however any suitable spacing distance which allows for sufficient suctioning of collected fluid during filtration is felt to fall within the scope of the present invention.

Referring back to FIGS. 3 and 5, the functional aspects of valve cap 38 will be discussed. Valve cap 38 serves as a retaining member for securing the proximal end of drop tube 31 to filter assembly 37 and also functions as a one way valve. The one-way valve action of valve cap 38 permits the reflux of trapped air or blood that has developed clots after filtration by fine filter 21 back into the collection chamber 16. This reflux action clears out the blood clots and trapped air from the fluid pathway leading from fine filter 21. According to the present invention, the fluid pathway comprises the conduit through drop tube 31 inside collection chamber 16 and the portion of infusion tubing 15 interposed between the outlet port 22 of CDU 12 and the patient 13.

Figure 7:
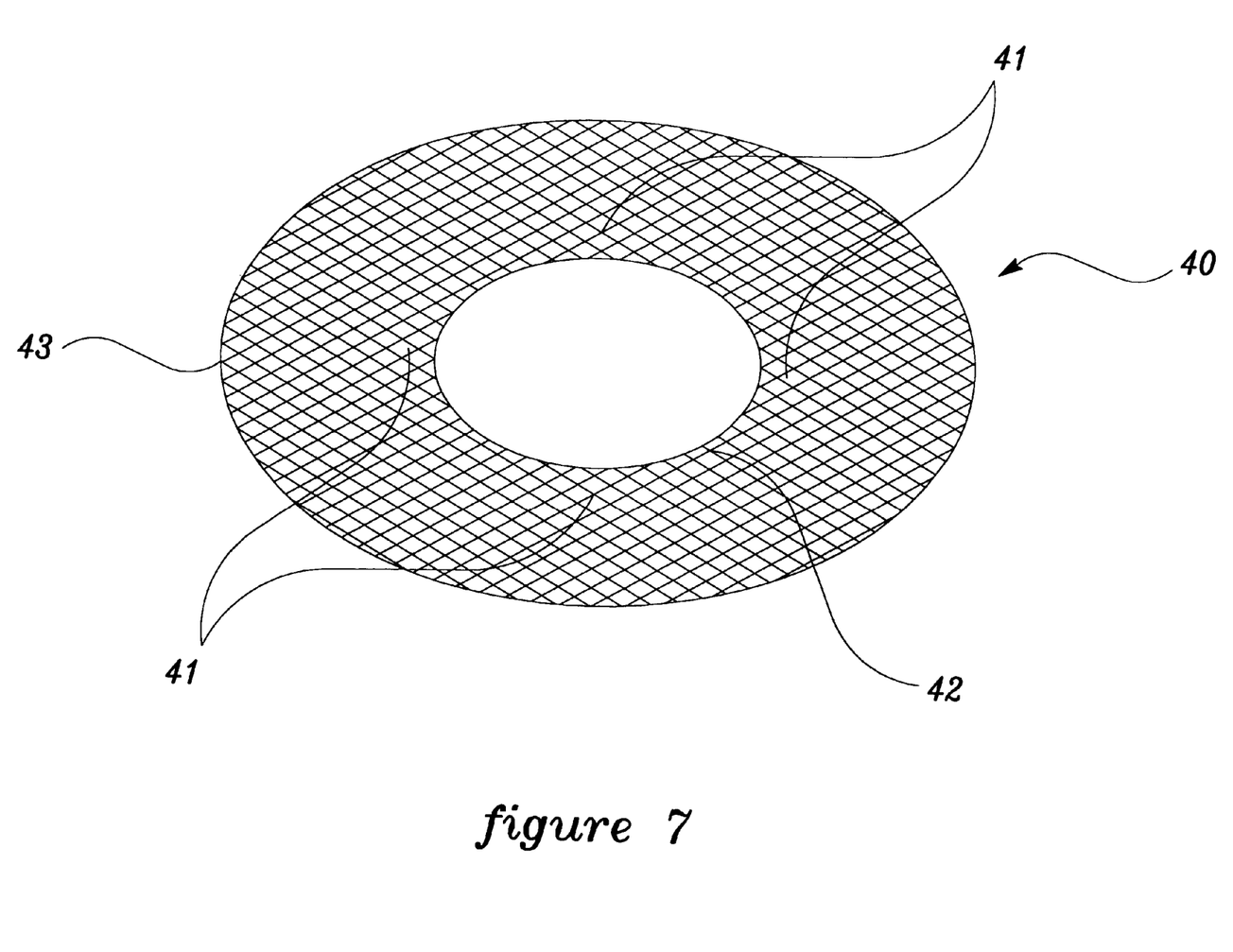
FIG. 7 is a perspective view of the filter disc according to the present invention.

To facilitate the reflux action, valve cap 38 includes a filter disc 40 that is similar to the micron polyester screen 39 disclosed above. As best illustrated in FIG. 7, filter disc 40 has a donut shaped configuration and is bonded to the partition member 46 at a plurality of points 41 near the inner circumference 42 of disc 40. Whenever clots form or air becomes trapped inside drop tube 31 or tubing 15 after passing through fine filter 21, filter disc 40 functions as a one way valve. The flexibility of the polyester screen 39 of filter disc 40 permits the outer circumference 43 of disc 40 to lift up and allow clotted blood or trapped air to be flushed back into collection chamber 16 whenever a reflux action is initiated by the practitioner. This reflux action is initiated by the practitioner who places a syringe or other type of flushing means (not shown) in fluid flow communication with infusion tubing 15 attached to outlet port 22.

Figure 8:
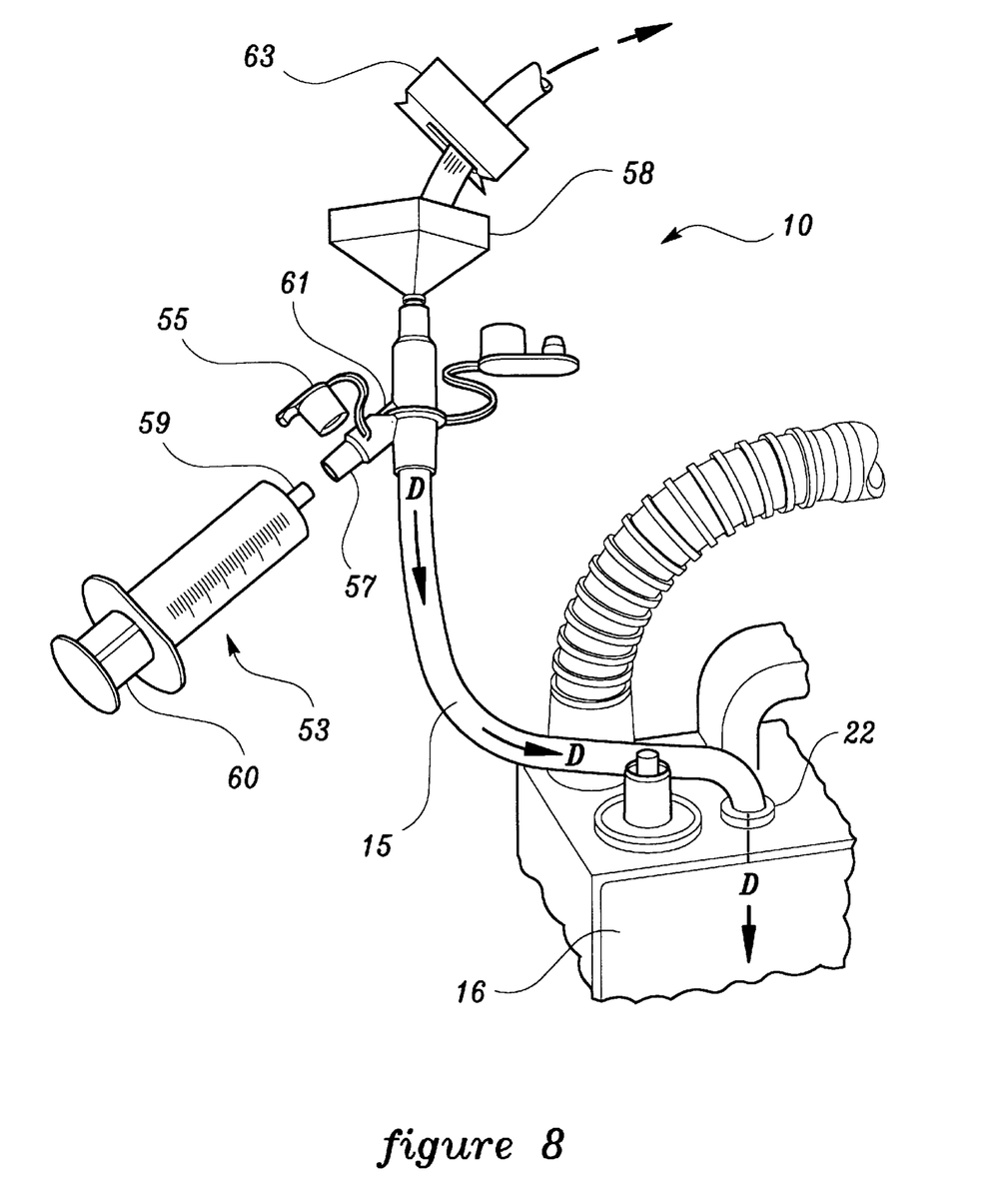
FIG. 8 is a perspective demonstrating the related method of using a standard luer tip syringe for flushing blood clots in the fluid pathway back into the collection chamber.

Referring now to FIGS. 3 and 8, the preferred method of clearing the fluid pathway of blood clots and trapped air inside autotransfusion system 11 will now be discussed in greater detail. The method of flushing out large blood clots and trapped air from the fluid pathway is initiated by the practitioner turning off infusion pump 14 so that fluid flow in the direction of patient 13 is interrupted. After infusion pump 14 is turned off, a slide clamp 63 is used to pinch off infusion tubing 15 downstream of microaggregate filter 58 from fluid flow communication therethrough. The practitioner then uncaps dust cap/plug combination 55 and inserts a luer tip 59 of flushing means 53 inside a spike valve 57 that is in fluid flow communication with the fluid pathway through Y-Site connector 54. In the preferred embodiment, spike valve 57 is a BESPAK valve manufactured by Bespak of Cary, N.C. The description of the BESPAK valve is disclosed in the applicant's co-pending U.S. patent application No. 08/481,237 entitled "Spike Port with Integrated Two Way Valve Access", the entire disclosure herein incorporated by reference in its entirety. Preferably, the flushing means 53 is a syringe that includes a plunger 60 and luer tip 59 and contains a solution of sterile saline, however any suitable type of flushing means that forces a fluid medium through the fluid pathway in a clearing action is felt to fall within the scope of the present invention.

Once the luer tip 59 is inserted and engaged to spike valve 57 and plunger 60 is in the full pull back position, the practitioner pushes plunger 60 forward until all of the saline is released into the fluid pathway. The release of the saline forces any blood clots or trapped air back through the fluid pathway in the direction denoted by fluid flow D.

Referring back to FIG. 9, a more detailed description of the aforementioned flushing action in relation to valve cap 38 will be discussed in greater detail. After the practitioner has initiated the flushing action in the direction of fluid flow D, blood clots and trapped air contaminating the blood are forced back through the fluid pathway and into collection chamber 16 through outlet port 22. Once through outlet port 22, the contaminated blood travels through drop tube 31 where it exits at collection opening 51 and into an interior chamber 62 of filter assembly 37. This flushing action produces a positive pressure within filter assembly 37 which forces open the outer circumference 43 of filter disc 40 in a flapping action that forces out the contaminated blood back into collection chamber 16 while also producing a limited fluid flow through the filter media 39. After the flushing action has subsided, outer circumference 43 is restored to its original resting position, whereby the polyester screen 39 of filter disc 40 will function as a filtration site, along with fine filter 21, to refilter the contaminated blood.

In cases where the microaggregate filter 58 becomes occluded due to contaminated blood, the practitioner must remove filter 58 after first turning off infusion pump 14. Once microaggregate filter 58 is detached and the above procedure is competed, the practitioner can then replace filter 58 with a new one and the autotransfusion-procedure may be re-started.

Although particular embodiments of the invention have been shown, it is not intended that the invention be limited thereby, instead, the scope of the present invention is intended to be limited only by the appended claims.

What is claimed is:

1. A method of clearing a fluid pathway of an autotransfusion system of blood clots and other contaminants, the autotransfusion system including a valve, said valve being disposed within a collection chamber including a top wall, said top wall having an opening being in fluid flow communication with tubing attached to a patient, said valve being in fluid flow communication with a fluid pathway that leads to a patient through said tubing, said tubing having a spike port in fluid flow communication thereto, comprising the steps of:

a) providing a user with an injection means containing a fluid;

b) closing off the portion of said tubing leading to a patient from fluid flow therethrough;

c) engaging said injection means to said spike port and injecting said fluid into said fluid pathway, whereby said fluid forces back blood clots and other contaminants in said fluid pathway through said valve and back into said collection chamber.

2. The method according to claim 1, wherein said injection means is a syringe, said syringe having a distal end and a proximal end, said distal end forming an aperture for fluid flow therethrough, said proximal end including a plunger for injecting said fluid through said aperture.

3. The method according to claim 1, wherein the said step of engaging further includes inserting said aperture of said injection means into said spike port.

* * * * *